(12) United States Patent
Giudiceandrea

(10) Patent No.: US 8,509,491 B2
(45) Date of Patent: Aug. 13, 2013

(54) PROCESS FOR CHECKING THE QUALITY OF LOGS

(75) Inventor: Federico Giudiceandrea, Bressanone (IT)

(73) Assignee: Microtec S.R.L., Bressanone (IT)

( * ) Notice: Subject to any disclaimer, the term of this patent is extended or adjusted under 35 U.S.C. 154(b) by 934 days.

(21) Appl. No.: 12/525,447

(22) PCT Filed: Oct. 30, 2007

(86) PCT No.: PCT/IT2007/000757
§ 371 (c)(1),
(2), (4) Date: Jul. 31, 2009

(87) PCT Pub. No.: WO2008/093374
PCT Pub. Date: Aug. 7, 2008

(65) Prior Publication Data
US 2010/0098298 A1    Apr. 22, 2010

(30) Foreign Application Priority Data

Feb. 2, 2007    (IT) .............................. VR2007A0018

(51) Int. Cl.
*G06K 9/00*    (2006.01)
(52) U.S. Cl.
USPC .......................................... 382/110; 382/100
(58) Field of Classification Search
USPC ......................................... 382/100, 110, 154
See application file for complete search history.

(56) References Cited

U.S. PATENT DOCUMENTS

| 4,152,767 | A | * | 5/1979 | Laliotis | 356/635 |
|---|---|---|---|---|---|
| 5,257,101 | A | * | 10/1993 | Lee | 348/95 |
| 5,267,018 | A | * | 11/1993 | Kauppinen | 356/627 |
| 5,394,342 | A | * | 2/1995 | Poon | 702/137 |
| 5,644,392 | A | * | 7/1997 | Soest et al. | 356/237.1 |
| 6,122,065 | A | * | 9/2000 | Gauthier | 356/394 |
| 6,474,379 | B1 | * | 11/2002 | Mellor et al. | 144/357 |

(Continued)

FOREIGN PATENT DOCUMENTS

| DE | 100 64 891 A1 | 6/2002 |
|---|---|---|
| EP | 1 729 116 A1 | 12/2006 |
| WO | 2004/083778 A1 | 9/2004 |

OTHER PUBLICATIONS

"Screenlog—The 360 degree Log Viewer", Internet Citation, [Online] 2004, XP002393700, Retrieved from the Internet: URL:http://www.barrmullin.com/MiCROTEC/SCREENLOG.htm> [retrieved on Aug. 7, 2009].

(Continued)

*Primary Examiner* — Shefali Goradia
(74) *Attorney, Agent, or Firm* — Pearne & Gordon LLP

(57) ABSTRACT

A process for checking the quality of logs, each log having a front surface (2), a rear surface (6) and a lateral surface (3). In the process, the quality check being carried out by means of a visual examination of the outer appearance of the logs (1). The process also comprising the operating steps of obtaining a first flat photographic representation (7) which represents the flat extension of the lateral surface (3) of the log (1), and if necessary a second flat photographic representation (4) which represents the front surface (2) of the log (1), and a third flat photographic representation (5), representing a rear surface (6) of the log (1). Finally, the quality of the log (1) is evaluated by means of an examination of the photographic representations (4), (5), (7).

28 Claims, 3 Drawing Sheets

(56) References Cited

U.S. PATENT DOCUMENTS

| | | | |
|---|---|---|---|
| 6,597,761 B1 | 7/2003 | Garms, III | |
| 6,757,354 B2* | 6/2004 | Skatter et al. | 378/58 |
| 7,406,190 B2* | 7/2008 | Carman et al. | 382/141 |
| 8,155,426 B2* | 4/2012 | Paavola | 382/141 |
| 2007/0286474 A1* | 12/2007 | Dralle | 382/154 |

OTHER PUBLICATIONS

"DiSHAPE—Three-Dimensional Reality", Internet Citation, [Online] 2004, XP002393701, Retrieved from the Internet: URL:http://www.barrmullin.com/MiCROTEC/DiSHAPE.htm> [retrieved on Aug. 7, 2006].

* cited by examiner

– 1 –
PROCESS FOR CHECKING THE QUALITY OF LOGS

TECHNICAL FIELD

The present invention relates to a process for checking the quality of logs based on an examination of their outer appearance.

BACKGROUND ART

When processing wood the best possible knowledge of each log 1 is essential to identify its optimum use. This requires a combination of several pieces of information: geometric structure of the log 1, presence of surface or inner defects, log 1 coefficient of elasticity, etc. The price of the log 1 may vary considerably based on these parameters.

To identify any defects one of the methods that can be used involves visual inspection of the log 1 so as to detect the presence of knots, cracks, etc.

Therefore, at present, when the quality of a log 1 has to be checked, a skilled operator carefully examines its outer surface (both the lateral surface and the surface of the two ends). Given the extended form of the log 1, the operator may either move all the way around the log 1, or observe it with the aid of mirrors positioned around it.

However, this known technology has several disadvantages.

Firstly, it is often impossible to examine the lower part of the log 1 on which it rests.

Secondly, the live visual inspection is a relatively lengthy process.

In addition, the analysis performed in this way is decisively affected by the capabilities of the operator, who must be able to analyse the log 1 in the best possible way in the shortest possible time, in particular where he can count only on reflected images which, inevitably, are affected by the substantially cylindrical shape of the log 1.

This method is also affected by any differences in lighting of the surface of the log 1 which may arise in the working environment.

The same type of problem occurs in general with all types of wood. However, as regards boards whose walls are all flat, this has been solved using algorithms (known), able to automatically examine the photographs of the various surfaces of the boards.

However, that method is not directly applicable to the case of logs because, with logs, any photograph of the lateral surface is affected by the curvature of the log 1 which distorts the view of it.

DISCLOSURE OF THE INVENTION

In this situation, the technical purpose which forms the basis of the present invention is to provide a process for checking the quality of logs which overcomes the above-mentioned disadvantages.

In particular the technical purpose of the present invention is to provide a process for checking the quality of logs which allows the entire surface of the log 1 to be checked easily.

The present invention also has for a technical aim to provide a process for checking the quality of logs which allows an easy and safe evaluation.

The present invention also has for a technical aim to provide a process for checking the quality of logs which allows an automated evaluation.

The technical purpose specified and the aims indicated are substantially achieved by a process for checking the quality of logs as described in the claims herein.

BRIEF DESCRIPTION OF THE DRAWINGS

Further features and advantages of the present invention are more apparent in the detailed description below, with reference to several preferred, non-limiting embodiments of a process for checking the quality of logs, illustrated in the accompanying drawings, in which.

DETAILED DESCRIPTION OF THE PREFERRED EMBODIMENTS OF THE INVENTION

Figure 1:
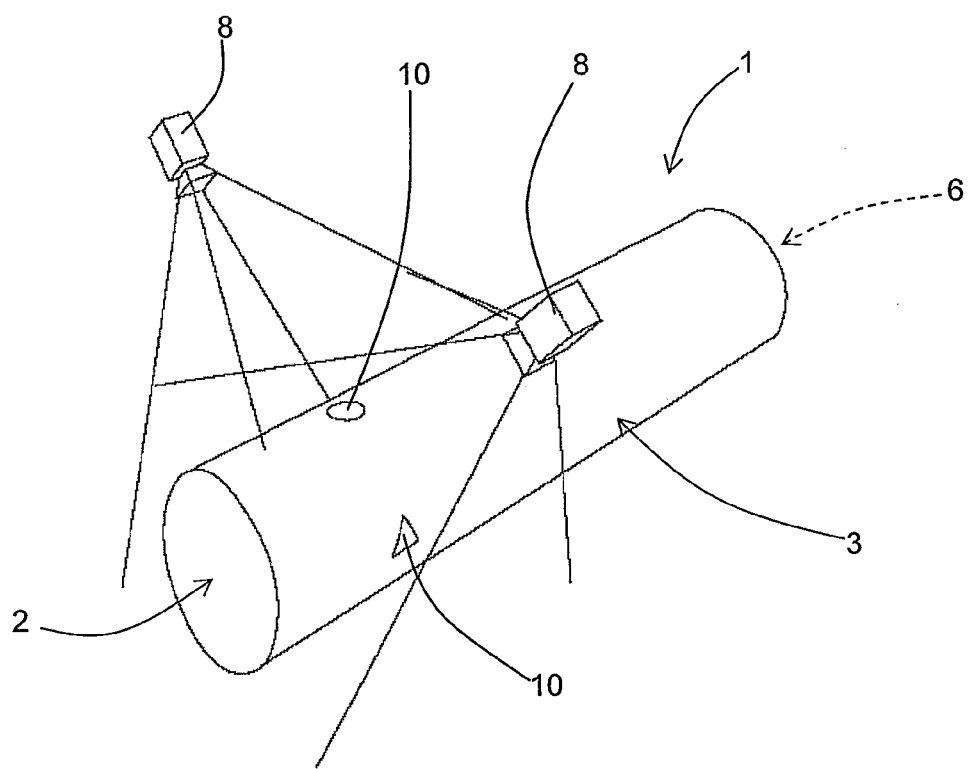
FIG. 1 is a schematic axonometric view of a part of a station for photographing a log 1.
Figure 2:
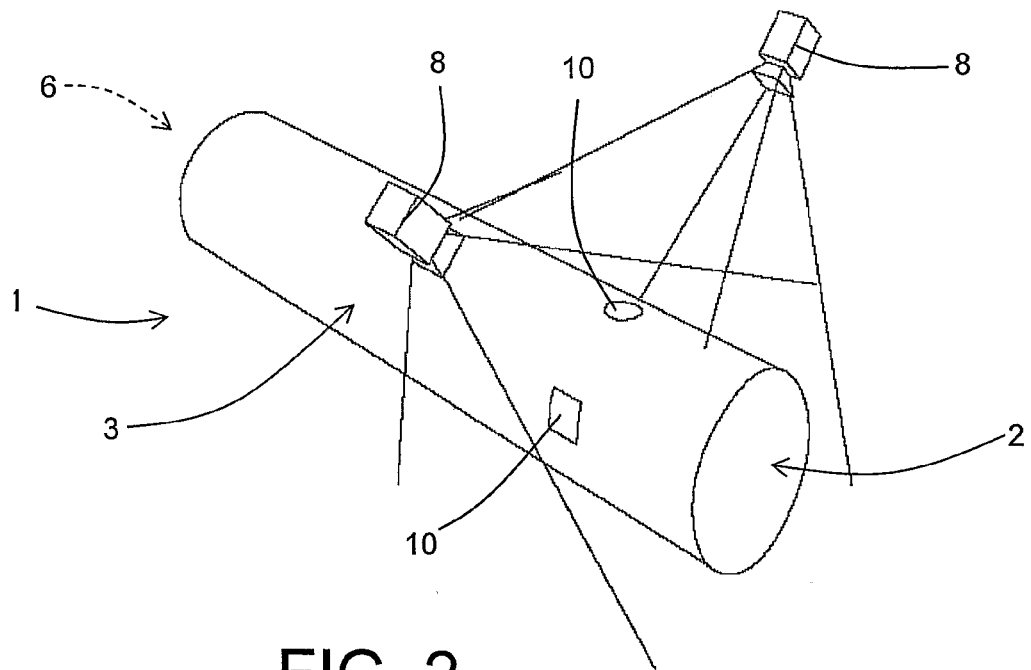
FIG. 2 illustrates another part of the photographing station of FIG. 1.
Figure 3:
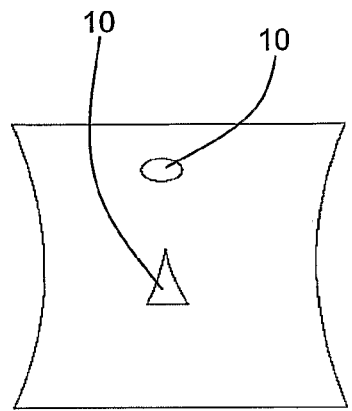
FIG. 3 is a schematic view of the image photographed by the part of the station of FIG. 1.
Figure 4:
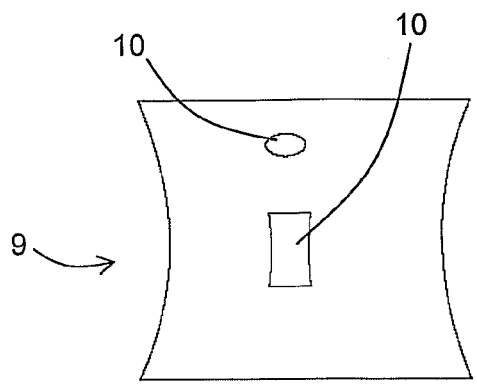
FIG. 4 is a schematic view of the image photographed by the part of the station of FIG. 2.
Figure 5:
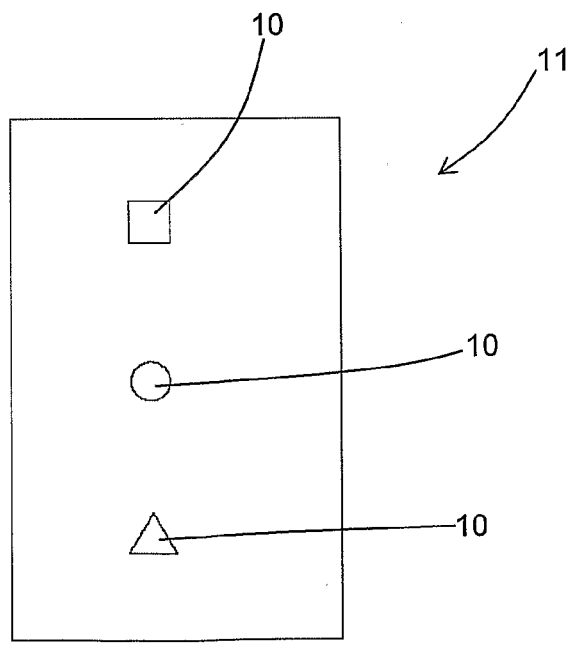
FIG. 5 shows an image which can be obtained by combining the images of FIGS. 3 and 4.
Figure 6:
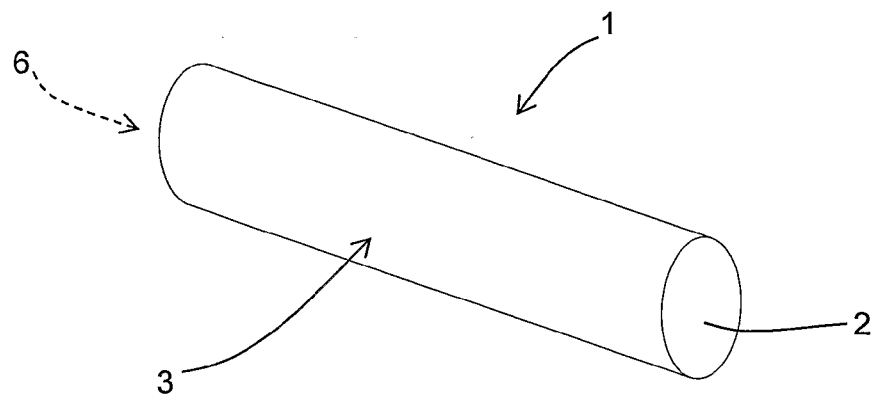
FIG. 6 is a schematic axonometric view of a log 1.

The process for checking the quality of logs in accordance with the present invention is based, like the prior art processes, on the evaluation of the outer appearance of the logs 1, and in particular, of their front surfaces 2 and rear surfaces 6 which represent the inner section of the log 1, and their lateral surfaces 3.

Figure 7:
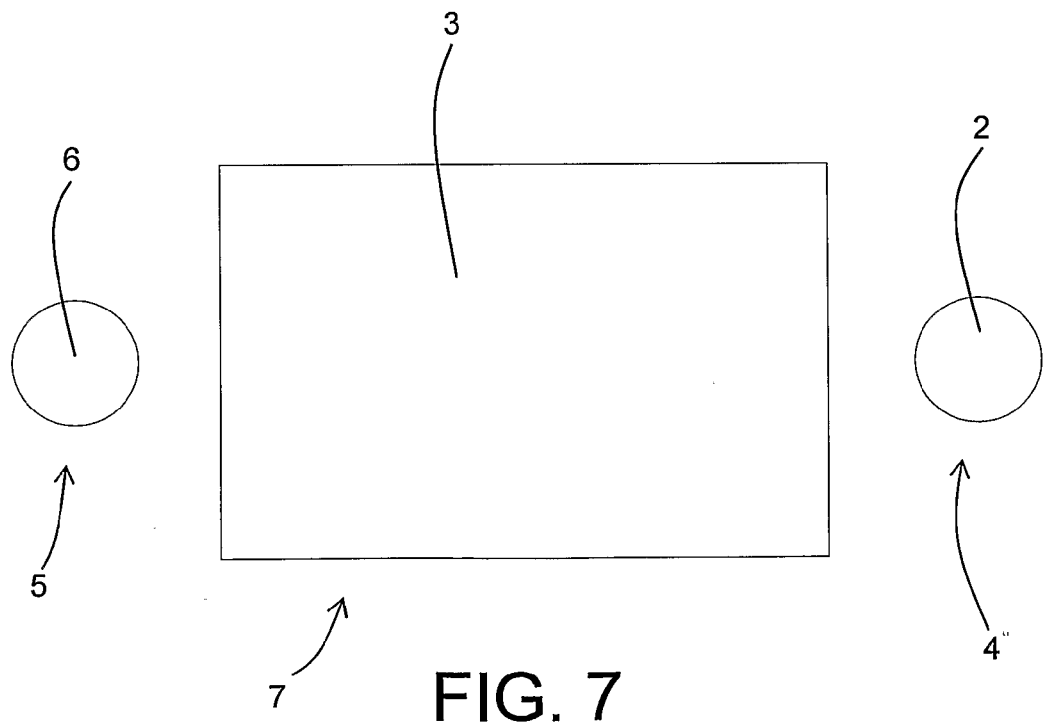
FIG. 7 shows three photographic reproductions representing the entire surface of the log 1 of FIG. 6, in accordance with the present invention.

However, in accordance with the present invention, the process involves a first step of obtaining a first flat photographic representation 7 which represents the flat extension of the lateral surface 3 of the log 1, and if necessary a second step of obtaining a second flat photographic representation 4 which represents the front surface 2 of the log 1, and a third step of obtaining a third flat photographic representation 5, in turn representing the rear surface 6 (FIG. 7).

Advantageously, the three steps described may be carried out in any order, since they are independent of one another.

Once each of the above-mentioned photographic representations 4, 5, 7 has been obtained, the process disclosed involves examining each photographic representation to evaluate the quality of the log 1. In particular, in the simplest embodiment of the present invention, at least the first photographic representation is examined.

In the various embodiments there are two main methods for evaluating the quality.

According to a first method, the evaluation is carried out by a skilled operator who directly observes the photographic representations 4, 5, 7 which, for that purpose, may be presented on a specific monitor. In this case, the monitor will be controlled by an electronic system which can also be provided with any additional functions required, such as the possibility of zooming on specific parts of each photographic representation. Moreover, the electronic system may be programmed to send the photographs on the monitor using predetermined methods. For example, it may be possible for the three photographic representations 4, 5, 7 to be reproduced on the monitor one after another, or for the first photographic representation 7, which usually has a longitudinal extension much greater than the transversal dimension, to be "scrolled" on the monitor so that the inspection of the surface is carried out as if the operator were moving along the log 1.

In contrast, in the more complex embodiments, the evaluation of log 1 quality is automated, performed directly by a computer. For this purpose, thanks to the fact that modified views of the log 1 are available which represent it as if it were an object with flat faces, the computer can analyse each photographic representation using one or more analysis algorithms similar to those currently used to evaluate wooden boards.

Without changing the core of the invention described above, depending on the embodiments, the methods with which the three photographic representations 4, 5, 7 are obtained may vary (in particular with reference to the first photographic representation 7).

Depending on requirements, the three photographic representations 4, 5, 7 may be obtained either directly at the moment when the log 1 visual quality evaluation has to be carried out, or earlier, being saved electronically. In the latter case, when log 1 quality has to be evaluated, the photographic representations can easily be retrieved from the electronic system which manages everything.

In general, the second and the third 5 flat photographic representations are obtained by frontal photography respectively of the front surface 2 and the rear surface 6 of the log 1, since they are two substantially flat surfaces.

Since the shape of the lateral surface 3 of the log 1 is roughly like that of a cylinder, the first photographic representation 7 is obtained by taking several photographs of the log 1 lateral surface 3 and combining the photographs obtained in this way so as to take into consideration the deformation due to the curvature of the log 1.

Said circumstance is schematically illustrated in FIGS. 1 to 4 which show how, at a predetermined station, two separate cameras 8 photograph the surface of the log 1, obtaining two images 9 in which the central part corresponds to the actual appearance of the surface of the log 1 in that zone, whilst the upper and lower parts represent a distorted view of it. This effect was highlighted with geometrical FIG. 10 present on the log 1. As shown, following the distortion, the circle is seen as an ellipse and the square and the triangle are deformed.

Therefore, at this point the two images 9 have to be electronically combined, using known algorithms, to obtain a flat photographic representation 11 in which every point is presented as it would be presented if seen on the log 1 from a viewpoint radially outside it.

In some embodiments, for each log 1 there is a computerised three-dimensional model of it available, with which a three-dimensional photographic image is also associated.

In this case, to obtain the first flat photographic representation 7 it is sufficient to retrieve the three-dimensional computerised model of the log 1 with the associated three-dimensional photographic view of the lateral surface 3 of the log 1, and, again electronically, extend in a plane the photographic representation of the lateral surface 3 of the three-dimensional model.

Depending on requirements, the computerised three-dimensional model may also be obtained during another operating step of detecting the three-dimensional structure of the log 1, although this is a prior art step (for example, it may use known laser triangulation principles).

Once the three-dimensional model of a log 1 has been obtained, and the complete photographic representation of the log 1, the two can be associated, as described in European patent application number 06 113 317.9 in the name of the same Applicant, whose relative content is incorporated here by way of reference, thus defining the correspondence in space between the photographed points and the points of the three-dimensional model.

The present invention brings important advantages.

Thanks to this invention, the quality of the entire surface of the log can easily be checked without any blind spots.

Moreover, even if performed by an operator, the evaluation is easier and safer than prior art evaluations, because the operator can observe the entire surface of the log from the best viewpoint without having to move.

Also, this observation is not affected by any differences in log lighting, because when the photographs are taken, the log is evenly lit.

In addition, thanks to the fact that the photographic representation of the lateral surface of the log extends in such a way that it is flat, automated log quality checking is also possible.

It should also be noticed that the present invention is relatively easy to produce and even the cost linked to implementation of the invention is not very high.

The invention described above may be modified and adapted in several ways without thereby departing from the scope of the inventive concept.

All details of the invention may be substituted by other technically equivalent elements and, in practice, all of the materials used, as well as the shapes and dimensions of the various components, may be any according to requirements.

The invention claimed is:

1. A process for checking the quality of a log, the log having a front surface surrounded by a front surface perimeter, a rear surface surrounded by a rear surface perimeter, and a lateral surface, the lateral surface being the surface of the log between the front surface perimeter and the rear surface perimeter, the lateral surface having a substantially curved shape of a log, the quality check being carried out via a visual examination of the outer appearance of the log, characterised in that the process comprises the operating steps of:
    (a) obtaining a first flat photographic representation, representing the flat extension of the whole lateral surface of the log and in which every point is presented as it would be presented if seen on the log from a viewpoint positioned outside the log along a direction which extends radially from the log and passes through the point, said first flat photographic representation having been obtained via use of one or more cameras; and
    (b) evaluating the quality of the log by examining the first photographic representation.

2. The process according to claim 1, characterised in that it also comprises the operating step of obtaining a second flat photographic representation, representing the front surface of the log, and also being characterised in that the quality of the log is also evaluated by examining the second photographic representation.

3. The process according to claim 2, characterised in that it also comprises the operating step of obtaining a third flat photographic representation, representing the rear surface of the log, and also being characterised in that the quality of the log is also evaluated by examining the third photographic representation.

4. The process according to claim 3, characterised in that the third flat photographic representation is obtained by means of frontal photography of the rear surface of the log.

5. The process according to claim 2, characterised in that the evaluation is carried out by an operator observing the photographic representations.

6. The process according to claim 5, characterised in that the photographic representations are presented on a monitor and also being characterised in that the operator observes the photographic representations on the monitor.

7. The process according to claim 2, characterised in that the evaluation step is carried out in an automated fashion by a computer.

8. The process according to claim 7, characterised in that the evaluation step involves analysis of each photographic representation using one or more analysis algorithms.

9. The process according to claim 2, characterised in that the second flat photographic representation is obtained by means of frontal photography of the front surface of the log.

10. The process according to claim 1, characterised in that the evaluation is carried out by an operator observing the first photographic representation.

11. The process according to claim 10, characterised in that the photographic representation is presented on a monitor and also being characterised in that the operator observes the photographic representation on the monitor.

12. The process according to claim 10, characterised in that the first flat photographic representation is obtained by taking several photographs of the lateral surface of the log and combining the photographs obtained in this way.

13. The process according to claim 10, characterised in that obtaining the first flat photographic representation involves the operating steps of:
   taking a three-dimensional computerised model of the log with the associated three-dimensional photographic view of the appearance of the lateral surface of the log; and
   extending in a plane the photographic representation of the lateral surface of the three-dimensional model.

14. The process according to claim 13, characterised in that it also comprises an operating step of preparing the three-dimensional computerised model, and a step of associating the photographic view of the outer appearance with the lateral surface of the three-dimensional model.

15. The process according to claim 14, characterised in that the association step involves the operating steps of photographing the log according to a plurality of different viewpoints, and identifying the spatial correspondence between the photographed points and the points of the three-dimensional model.

16. The process according to claim 14, characterised in that the step of preparing the three-dimensional computerised model involves detecting the three-dimensional structure of the log.

17. The process according to claim 1, characterised in that the evaluation step is carried out in an automated fashion by a computer.

18. The process according to claim 17, characterised in that the evaluation step involves analysis of the photographic representation using one or more analysis algorithms.

19. The process according to claim 17, characterised in that the first flat photographic representation is obtained by taking several photographs of the lateral surface of the log and combining the photographs obtained in this way.

20. The process according to claim 17, characterised in that obtaining the first flat photographic representation involves the operating steps of:
   taking a three-dimensional computerised model of the log with the associated three-dimensional photographic view of the appearance of the lateral surface of the log; and
   extending in a plane the photographic representation of the lateral surface of the three-dimensional model.

21. The process according to claim 20, characterised in that it also comprises an operating step of preparing the three-dimensional computerised model, and a step of associating the photographic view of the outer appearance with the lateral surface of the three-dimensional model.

22. The process according to claim 21, characterised in that the association step involves the operating steps of photographing the log according to a plurality of different viewpoints, and identifying the spatial correspondence between the photographed points and the points of the three-dimensional model.

23. The process according to claim 21, characterised in that the step of preparing the three-dimensional computerised model involves detecting the three-dimensional structure of the log.

24. The process according to claim 1, characterised in that the first flat photographic representation is obtained by taking several photographs of the lateral surface of the log and combining the photographs obtained in this way.

25. The process according to claim 1, characterised in that obtaining the first flat photographic representation involves the operating steps of:
   taking a three-dimensional computerised model of the log with the associated three-dimensional photographic view of the appearance of the lateral surface of the log; and
   extending in a plane the photographic representation of the lateral surface of the three-dimensional model.

26. The process according to claim 25, characterised in that it also comprises an operating step of preparing the three-dimensional computerised model, and a step of associating the photographic view of the outer appearance with the lateral surface of the three-dimensional model.

27. The process according to claim 26, characterised in that the association step involves the operating steps of photographing the log according to a plurality of different viewpoints, and identifying the spatial correspondence between the photographed points and the points of the three-dimensional model.

28. The process according to claim 26, characterised in that the step of preparing the three-dimensional computerised model involves detecting the three-dimensional structure of the log.

\* \* \* \* \*